United States Patent
Xue

(10) Patent No.: US 10,842,788 B2
(45) Date of Patent: Nov. 24, 2020

(54) APPLICATION OF LEVOROTATORY TETRAHYDROPALMATINE TO THE TREATMENT OF DEPRESSION DISORDERS, BIPOLAR AND RELATED DISORDERS, AND MANIC EPISODES

(71) Applicant: Hong Xue, Hong Kong (CN)

(72) Inventor: Hong Xue, Hong Kong (CN)

(73) Assignee: PharmacoGenetics Limited, Shatin (HK)

( * ) Notice: Subject to any disclaimer, the term of this patent is extended or adjusted under 35 U.S.C. 154(b) by 0 days.

(21) Appl. No.: 16/516,870

(22) Filed: Jul. 19, 2019

(65) Prior Publication Data

US 2020/0022970 A1    Jan. 23, 2020

Related U.S. Application Data

(60) Provisional application No. 62/700,922, filed on Jul. 20, 2018.

(51) Int. Cl.
*A61K 31/473* (2006.01)
*A61K 9/00* (2006.01)
*A61P 25/24* (2006.01)
*A61P 25/18* (2006.01)
*A61P 25/22* (2006.01)

(52) U.S. Cl.
CPC .......... *A61K 31/473* (2013.01); *A61K 9/0014* (2013.01); *A61K 9/0053* (2013.01); *A61P 25/18* (2018.01); *A61P 25/22* (2018.01); *A61P 25/24* (2018.01)

(58) Field of Classification Search
CPC .............................. A61K 31/473; A61P 25/22
USPC .......................................................... 514/284
See application file for complete search history.

(56) References Cited

FOREIGN PATENT DOCUMENTS

WO    WO-2004087040 A2 * 10/2004 ......... A61K 31/4745

OTHER PUBLICATIONS

Lee, B., et al., "L-Tetrahydropalmatine Ameliorates Development of Anxiety and Depression-Related Symptoms Induced by Single Prolonged Stress in Rats," Biomolecules & Therapeutics, 2014, pp. 213-222, vol. 22, No. 3.

* cited by examiner

*Primary Examiner* — Kevin E Weddington
(74) *Attorney, Agent, or Firm* — Lewis Rice LLC

(57) ABSTRACT

The compound levorotatory-tetrahydropalmatine and pharmaceutical compositions thereof are provided for the treatment of 'depressant disorders', 'bipolar and related disorders', 'manic episodes' and 'anxiety disorders' as these disorders are defined in Diagnostic and Statistical Manual of Mental Disorders 5th Edition (DSM-5).

16 Claims, 9 Drawing Sheets

Lack of *l*-THP or *dl*-THP effects on locomotor activity.

|  | Locomotor Activity | | | |
|---|---|---|---|---|
| Treatment | Vehicle | *l*-THP | *dl*-THP | DZ |
| 0 | 296 ± 16.51 | - | - | - |
| 0.01 mg/kg | - | 254 ± 18.13 | 257 ± 20.64 | - |
| 0.05 mg/kg | - | 243 ± 21.46 | 253 ± 24.69 | - |
| 0.10 mg/kg | - | 227 ± 17.57 | 290 ± 21.97 | - |
| 0.50 mg/kg | - | 256 ± 29.21 | 290 ± 19.50 | - |
| 1.00 mg/kg | - | 221 ± 15.53 | 237 ± 23.58 | 275 ± 25.19 |
| 2.00 mg/kg | - | 234 ± 19.47 | 232 ± 19.57 | - |
| 2.50 mg/kg | - | 240 ± 13.81 | 274 ± 17.30 | - |
| 3.00 mg/kg | - | - | - | 215 ± 21.31* |

$n = 15 - 20$ mice/group. * $p < 0.05$.

Figure 8

Myorelaxant effects of *l*-THP and *dl*-THP based on horizontal wire test.

|  | No. of Falls | | | |
| --- | --- | --- | --- | --- |
| Treatment | Vehicle | *l*-THP | *dl*-THP | DZ |
| 0 | 0.4 ± 0.48 | - | - | - |
| 0.5 mg/kg | - | 0.40 ± 0.48 | 0.30 ± 0.48 | - |
| 1.0 mg/kg | - | 0.40 ± 0.48 | 0.50 ± 0.67 | - |
| 3.0 mg/kg | - | - | - | 7.10±0.87* |
| 5.0 mg/kg | - | 0.50 ± 0.67 | 0.40 ± 0.49 | - |
| 10.0 mg/kg | - | 1.00 ± 0.77 | 0.80 ± 0.64 | - |
| 30.0 mg/kg | - | 18.50 ± 3.54** | 21.60 ± 8.72** | - |

$n$ = 12-17 mice /group. *$p$ < 0.05, ** $p$ < 0.01.

Figure 9

APPLICATION OF LEVOROTATORY TETRAHYDROPALMATINE TO THE TREATMENT OF DEPRESSION DISORDERS, BIPOLAR AND RELATED DISORDERS, AND MANIC EPISODES

CROSS REFERENCE TO RELATED APPLICATIONS

This application claims the benefit of U.S. Provisional Patent Application Ser. No. 62/700,922 filed on Jul. 20, 2018, the disclosure of which is incorporated herein by reference in its entirety.

FIELD OF THE INVENTION

The invention relates to the use of levorotatory tetrahydropalmatine ("l-THP") as an agent for the treatment of bipolar disorder, depression and anxiety disorder.

BACKGROUND OF THE INVENTION

Depression is a state of low mood and aversion to activity. Anxiety disorder is anxiety heightened to an abnormal level, and includes panic disorder, social anxiety disorder and generalized anxiety disorder. Bipolar disorder (BD), which afflicts 3-5% of the population, is associated with mood variations and personality disorders, with lifetime rates for completed suicide 60 times higher than that for the general population (Leahy 2007). The life time cost of persons with onset of BD in 1998 in the US is estimated at 24 billion US dollars (Begley et al 2001). BD and major depressive disorder are both associated with interpersonal and social functioning (Depp et al 2010; Cusi et al 2012). Genomic analyses revealed association between Trpm2 gene (coding for a calcium ion-permeable cation channel) and BD, and Trpm2 sequence contained a D543E mutation in exon 11 and a R755C mutation in exon 15 (Kostyrko et al 2006; McQuillin et al 2006). Mice deficient in Trpm2 exhibited bipolar disease-related behavior of anxiety and decreased social responses measured based on Crawley's sociability and preference for social novelty test (Jang et al 2015). While the causations for these three major forms of mental illness are still poorly understood, their consequences on personal health and the burdens they impose on society are striking and urgently in need of effective treatments devoid of burdensome adverse side effects.

The medicinal herb Rhizoma *Corydalis yanhusuo* WT Wang has been employed with *Angelicae dahuricae* for reduction of pain (Yuan et al., 2004). It contains dl-tetrahydropalmatine ("dl-THP") which induces anxiolytic-like effects in mice when administered orally (Leung et al., 2003). The l-tetrahydropalmatine isomer ("l-THP") is a dopamine receptor antagonist with potential application to the treatment of drug addictions (Xu et al, 1989; Bei and Mantsch 2012; Liu et al 2009; Zhao et al, 2014). It is available in the Chinese pharmaceuticals market in the form of Rotundine tablets for analgesia and sedation under the regulation of Chinese Government with an oral dose of 60-120 mg, 1-4 times per day being a safe human dosage range. Recently, l-THP is also found to be effective for the treatment of posttraumatic stress disorder (PTSD) in mice at 50 mg/kg i.p. daily but not at 10 or 20 mg/kg i.p. daily. According to Diagnostic and Statistical Manual of Mental Disorders (DMS-5), PTSD is classified under the "Trauma- and Stressor-Related Disorders" chapter, distinct from chapters on "Depression Disorders", "Bipolar and Related Disorders" and "Anxiety Disorders".

SUMMARY OF THE INVENTION

The invention relates to the usage of levorotatory tetrahydropalmatine ("l-THP") as a therapeutic agent for the treatment of depression disorders, bipolar and related disorders and anxiety disorders.

The utility of l-THP for treatment of depression disorders is indicated by the finding that administration of low doses of l-THP to mice shorten significantly the immobility time of mice in the tail suspension test.

The utility of l-THP for treatment of bipolar and related disorders is indicated by the findings that administration of low doses of l-THP to mice induced anti-depression effect in shortening the immobility time of mice in the tail suspension test, increased social response behavior of mice based on Crawley's sociability and preference for social novelty tests performed with the three-chamber-box apparatus, and antimanic effects on amphetamine sensitized mice based on locomotor activity assessment. Anti-manic episode activity is also indicated by the antimanic effects.

The utility of l-THP for treatment of anxiety disorders is indicated by the finding that administration of low doses of l-THP to mice increase significantly the time spent in the open arms in the elevated plus-maze test.

A method for treating a depression disorder, a bipolar or bipolar-related disorder, a manic episode, or an anxiety disorder in a patient in need thereof is provided. The method comprises administering an effective amount to the patient of levorotatory-tetrahydropalmatine or a pharmaceutical composition comprising the effective amount of the levorotatory-tetrahydropalmatine.

Other objects and features will be in part apparent and in part pointed out hereinafter.

BRIEF DESCRIPTION OF THE DRAWINGS

FIG. 8 shows a table recording the effects of various oral doses of l-THP or dl-THP, or doses of diazepam (DZ) i.p. on the level of locomoter activity assessed using a locomotor apparatus where locomotor activity was monitored based on crossing of infrared beams by the mouse. n=15-20 mice per group. *p<0.05 and **p<0.01 indicate significant difference from vehicle-treated ("Veh") group.

FIG. 9 shows a table recording the myorelaxant effects of various oral doses of l-THP or dl-THP, or doses of diazepam (DZ) i.p. based on the number of falls made by the mouse in the horizontal wire test. n=12 mice per group; **p<0.01 indicates significant difference from vehicle-treated ("Veh") group.

DESCRIPTION OF THE PREFERRED EMBODIMENTS

Figure 1:
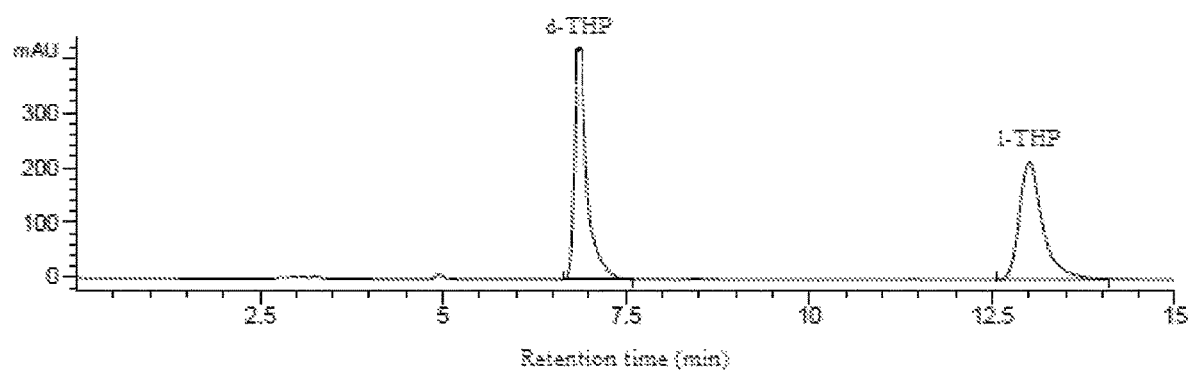
FIG. 1 shows high performance liquid chromatogram of dl-THP sample obtained from Indofine Chemical Co. NJ, USA. The d-THP and l-THP contents were determined based on area under UV absorbance curve expressed in millli-Abs unit (mAU) at 210 nm (y-axis) to comprise 51.0% d-THP and 49.0% l-THP.

In the invention, it has been discovered that l-THP and dl-THP, both constituents of Rhizoma Corydalis yanhusuo W. T. Wang (Y), significantly shorten the immobility time displayed by mice in the tail suspension test at an oral dose of 0.5-5.0 mg/kg for l-THP, and 2.0-5.0 mg/kg for dl-THP. These findings indicate that l-THP and dl-THP can be employed as antidepressant therapeutic agents for the treatment of depression disorders.

It has been discovered also that 0.1 mg/kg l-THP and 0.5 mg/kg l-THP significantly enhanced the sociability of mice in Crawley's sociability and preference for social novelty test, and that 0.1 mg/kg l-THP and 0.5 mg/kg l-THP significantly enhanced the preference for social novelty of mice in Crawley's sociability and preference for social novelty test.

It has been discovered also that 0.05 mg/kg, 0.1 mg/kg and 0.2 mg/kg l-THP significantly decreased the enhanced locomotor activity level of amphetamine sensitized mice. These findings together with the tail suspension test findings and the findings of enhancements of sociability and preference for social novelty described in the preceding sections indicate that l-THP can be employed as a therapeutic agent for the treatment of manic episodes and bipolar disorders.

It has been discovered also that 0.1 mg/kg-2.5 mg-kg l-THP significantly increased the time spent by mice in the open arms in the elevated plus-maze test. These findings indicated that l-THP can be employed as a therapeutic agent for the treatment of anxiety disorders.

Over the antidepressant oral dosages of l-THP and dl-THP tested, the social interaction enhancing oral dosages of l-THP tested, the oral antimanic dosages of l-THP tested, and the oral anxiolytic dosages of l-THP tested, neither l-THP nor dl-THP induced any significant change in the level of locomotor activity of the mice based on infrared-beam crossings, or any significant myorelaxant effect based on the number of falls made by the mice in the horizontal wire test.

A method is provided for treating a depression disorder, a bipolar or bipolar-related disorder, a manic episode, or an anxiety disorder in a patient in need thereof. The method comprises administering an effective amount to the patient of levorotatory-tetrahydropalmatine or a pharmaceutical composition comprising the effective amount of the levorotatory-tetrahydropalmatine.

As used herein, the terms "depression disorder," "bipolar disorder." "bipolar-related disorder," "manic episodes," and "anxiety disorder" are as defined in the Diagnostic and Statistical Manual of Mental Disorders, Fifth Edition, published by the American Psychiatric Association (2013) ("DSM-5"). It is noted that none of these disorders include post-traumatic stress disorder.

The term "treating" as used herein includes achieving a therapeutic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder.

As used herein, an "effective amount" is an amount effective to achieve therapeutic benefit. The actual amount effective for a particular application will depend on the patient (e.g., age, weight, etc.), the condition being treated, and the route of administration. Determination of an effective amount is well within the capabilities of those skilled in the art, especially in light of the disclosure herein. The effective amount for use in humans can be determined from animal models.

When used for treating a depression disorder, the effective amount of l-THP is preferably from about 2 mg to about 15 mg per kg body weight administered.

When used for treating a bipolar or bipolar-related disorder, the effective amount of l-THP is preferably from about 0.1 mg to about 15 mg per kg body weight administered.

When used for treating manic episode, the effective amount of l-THP is preferably from about 0.1 mg to 2 mg per kg body weight administered.

When used for treating an anxiety disorder, the effective amount of l-THP is from about 0.2 mg to 15 mg per kg body weight administered.

In any of the methods described herein, the patient may not be in need of treatment for post-traumatic stress disorder.

The effective amount of l-THP can be administered in a single aliquot, or in two or more aliquots.

The l-THP and dl-THP agents described herein can be delivered to the subject using a wide variety of routes or modes of administration, such as oral, transdermal (e.g., skin patch) and parenteral (e.g., intravenous or subcutaneous injection). The preferred routes for administration are the oral and transdermal routes.

The l-THP and dl-THP agents described herein may be formulated in a conventional manner as a pharmaceutical composition comprising the l-THP or dl-THP and one or more pharmaceutically acceptable excipients. Suitable excipients include carriers, diluents, and auxiliaries which facilitate processing of the active l-THP or dl-THP into preparations that can be used physiologically (see, e.g., Remington's Pharmaceutical Sciences).

The formulation of the composition is dependent upon the route of administration chosen. For oral administration, the compositions can be formulated readily by combining the composition with pharmaceutically acceptable excipients well known in the art. Such excipients enable the compositions to be formulated as tablets, pills, dragees, capsules, liquids, gels, syrups, slurries, suspensions, wafers, and the like, for oral ingestion by a subject to be treated. Suitable excipients are, in particular, fillers such as sugars, including lactose or sucrose; polymer preparations such as, for example, maize starch, wheat starch, rice starch, potato starch, gelatin, gum tragacanth, methyl cellulose, hydroxypropylmethyl-cellulose, sodium carboxymethylcellulose, and/or polyvinyl pyrrolidone (PVP); and various flavoring agents known in the art. If desired, disintegrating agents may be added, such as the cross-linked polyvinyl pyrrolidone, agar, or alginic acid or a salt thereof such as sodium alginate.

Having described the invention in detail, it will be apparent that modifications and variations are possible without departing from the scope of the invention defined in the appended claims.

EXAMPLES

The following non-limiting examples are provided to further illustrate the invention.

Example 1: Animal Preparation

Animal Preparation. Male ICR mice (20-35 g) supplied by the Animal and Plant Care Facility, HKUST) were housed in groups of five to ten with food and water ad lib, and kept on a 0800 hour to 2000 hour light cycle. All animal experiments were pre-approved by the HKUST Animal Ethics Committee in accordance with the Code of Practice for Care and Use of Animals for Experimental Purposes of Agriculture, Fisheries and Conservation Department and the Department of Health of the Hong Kong Special Administrative Region. All animal procedures were carried out in a quiet laboratory between 0800 h and 1300 h at an ambient temperature of 20-22° C. At the end of each test session, all items of apparatus were thoroughly cleaned with 80% ethanol.

Example 2: Tail Suspension Test

Tail suspension test. Male ICR mice 4 to 6 weeks of age were randomized into groups (n=12-20/group). Vehicle (0.9% NaCl), or one of oral l-THP, dl-THP and d-THP (0.1-5.0 mg/kg) was administered 45 minutes prior to testing; or 30 mg/kg oral imipramine was administered 30 minutes prior to testing. In the test, a mouse was taped to a bar by the tail and suspended 15 cm above ground for 6 minutes. The total time of immobility was scored manually from 2 to 6 min during the period of suspension. Decreased time of immobility is indicative of antidepressant effect (Stem et al, 1985). To test whether the antidepressant effect elicited by l-THP or dl-THP can be blocked by the benzodiazepine (BZ) binding site antagonist flumazenil, naïve male 4-6 week old mice were randomly separated into three groups (n=12-20/group). The first group received vehicle (p.o.) 45 minutes prior to test and flumazenil (1.25 mg/kg i.p) 15 minutes prior to test, the second group received l-THP (2.0 mg/kg, p.o) or dl-THP (2.0 mg/kg, p.o.) 45 minutes prior to test and vehicle (i.p) 15 minutes prior to test, and the third group received l-THP (2.0 mg/kg p.o) or dl-THP (2.0 mg/kg p.o) 45 minutes prior to test and flumazenil (1.25 mg/kg i.p) 15 minutes prior to experiment.

Figure 2:
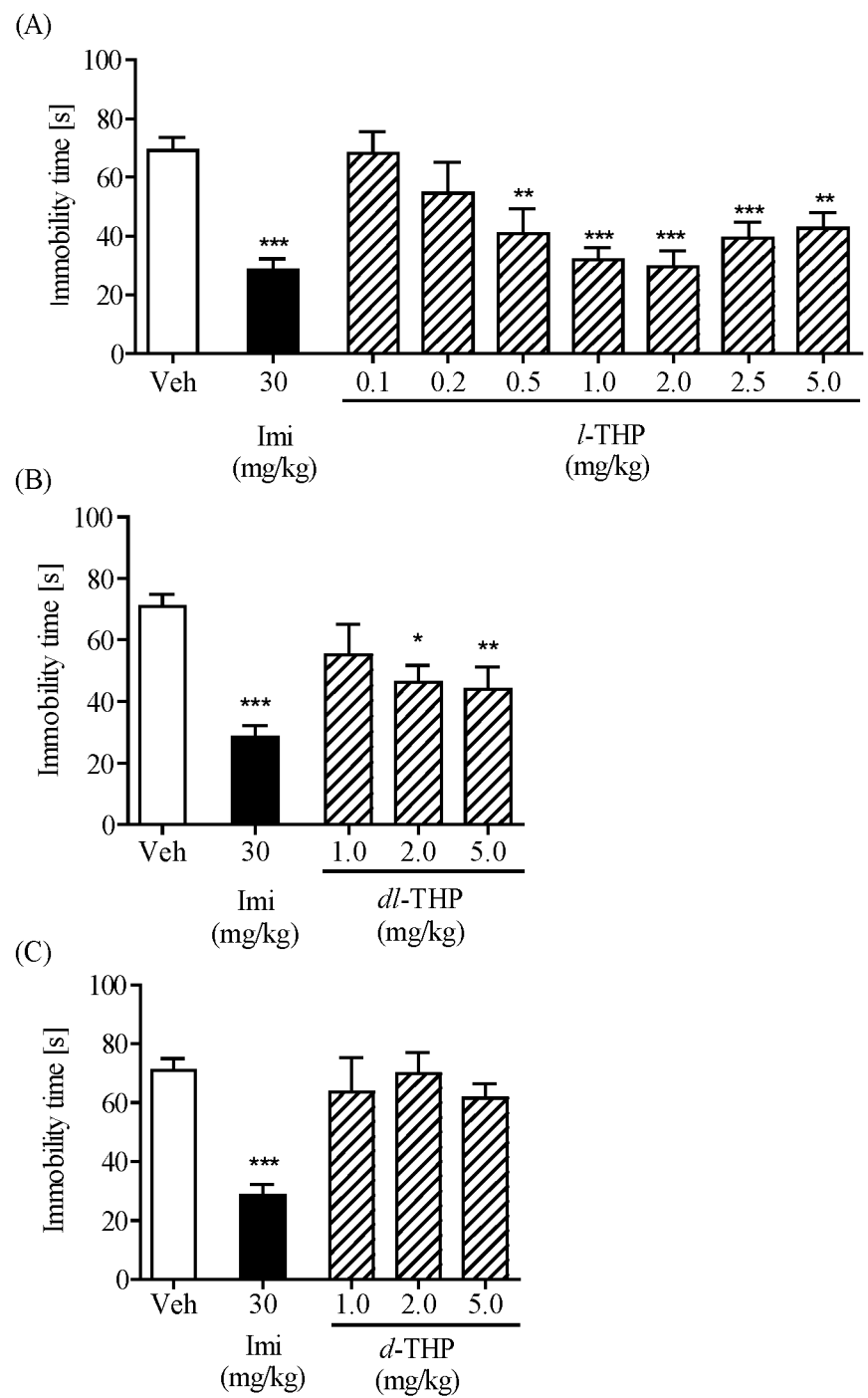
FIG. 2 shows bar graphs regarding the induction of antidepressant effects in mice based on the tail suspension test by (A) l-THP, (B) dl-THP and (C) d-THP. Data expressed as mean±S.E.M. of immobility time during a 4-minute test period monitored 45 minutes after the oral administration of l-THP, dl-THP or dl-THP (0.1-5.0 mg/kg), imipramine (Imi, 30 mg/kg) or vehicle (Veh, 0.9% NaCl), and shown as shaded, solid or open bars respectively. n=12-20 mice per group. $*p<0.05$, $p<0.01$ and $*p<0.001$ indicate significant difference from vehicle-treated ("Veh") group based on Newman-Keuls' test after one-way ANOVA.
Figure 6:
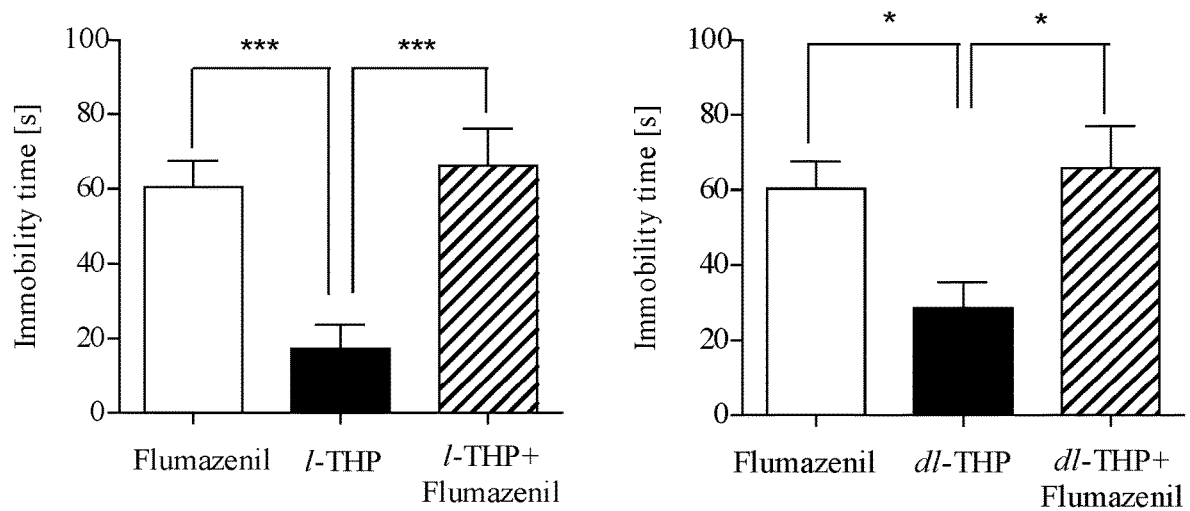
FIG. 6 shows bar graphs regarding the influence of flumazenil on antidepressant effects of l-THP and dl-THP based on immobility time in the tail suspension test. Data expressed as mean±S.E.M. of immobility time during a test period of 5 minutes. Where indicated, oral l-THP (2.0 mg/kg) or oral dl-THP (2.0 mg/kg) was administered 45 minutes prior to test period, whereas flumazenil (1.25 mg/kg, i.p.) was administered 15 minutes prior to test period. Open, solid and shaded bars represent mice receiving flumazenil i.p only, mice receiving oral l-THP or dl-THP only, and mice receiving flumazenil i.p. plus oral l-THP or dl-THP respectively. n=12-20 mice per group. *p<0.05 and ***p<0.001 indicate significant difference between two treatment groups joined by line based on Newman-Keuls' test after one-way Anova.

In the tail suspension test, l-THP induced a significant decrease in immobility time indicative of an antidepressant effect on the mice at dosages of 0.5 mg/kg-5.0 mg/kg (FIG. 2). By comparison, dl-THP also induced a significant decrease in immobility time, but only beginning at the higher dosage of 2.0 mg/kg. Imipramine (Imi), a tricyclic antidepressant drug, exhibited antidepressant effect at 30 mg/kg. The inhibition of the antidepressant effects of l-THP and dl-THP by the BZ-site antagonist flumazenil of $GABA_A$ receptors (FIG. 6) suggests the involvement of $GABA_A$ receptors in the antidepressant effects observed.

Example 3: Crawley's Sociability and Preference for Social Novelty Test

In Crawley's test, female ICR mice of 8 to 10 weeks were randomized into groups (n=12-20/group), and orally administered 45 minutes prior to testing with vehicle (0.9% NaCl), 0.1 mg/kg l-THP or 0.5 mg/kg l-THP. The test apparatus comprised a rectangular, three-chamber box. Each chamber was 19×45 cm, and the dividing walls between chambers were made of clear Plexiglas. The central chamber was connected to each side chamber with a removable wall. Two identical wire cylindrical containers with removable lids that were large enough to hold a single mouse each were placed vertically inside the apparatus, one in the middle of each side chamber. Each of these containers consisted of a cup made of metal wires to allow for air exchange between the interior and exterior of the cylinder but small enough to prevent direct physical interactions between an animal on the inside with one on the outside, and a removable lid. In the beginning of the test, the two cylindrical containers in the two side chambers were empty, and the subject mouse was placed at the center of the middle chamber for adaptation. After 5 minutes, one social-object mouse (stranger-1) was placed inside the cylinder in one of the side chambers. The placement of strange-1 was systematically changed between the two side chambers between trials. Then the walls separating the middle chamber from the two side chambers were removed to allow the subject mouse free access to all three chambers. In a first 10-minute session, the duration and number of direct contacts between the subject mouse and the container cup housing or not housing the stranger-1 mouse were recorded individually. At the end of this session, a second social-object mouse (stranger-2) was placed in the wire container cup that was empty during the first 10-minute session. Then the duration and number of direct contacts between the subject mouse and the two container cups holding stranger-1 mouse and stranger-2 mouse were recorded separately during a second 10-minute session. The first 10-minute session provided an estimate of the sociability of the subject mouse in terms of its preference if any to spend more time with the container holding the stranger-1 mouse compared to the empty container. The second 10-minute session provided an estimate of the preference of the subject mouse for social novelty in terms of its preference if any to associate with the container holding the novel stranger-2 mouse compared to the container holding the more familiar stranger-1 mouse (Moy et al 2004; Kaidanovich-Beilin et al., 2011).

Figure 3:
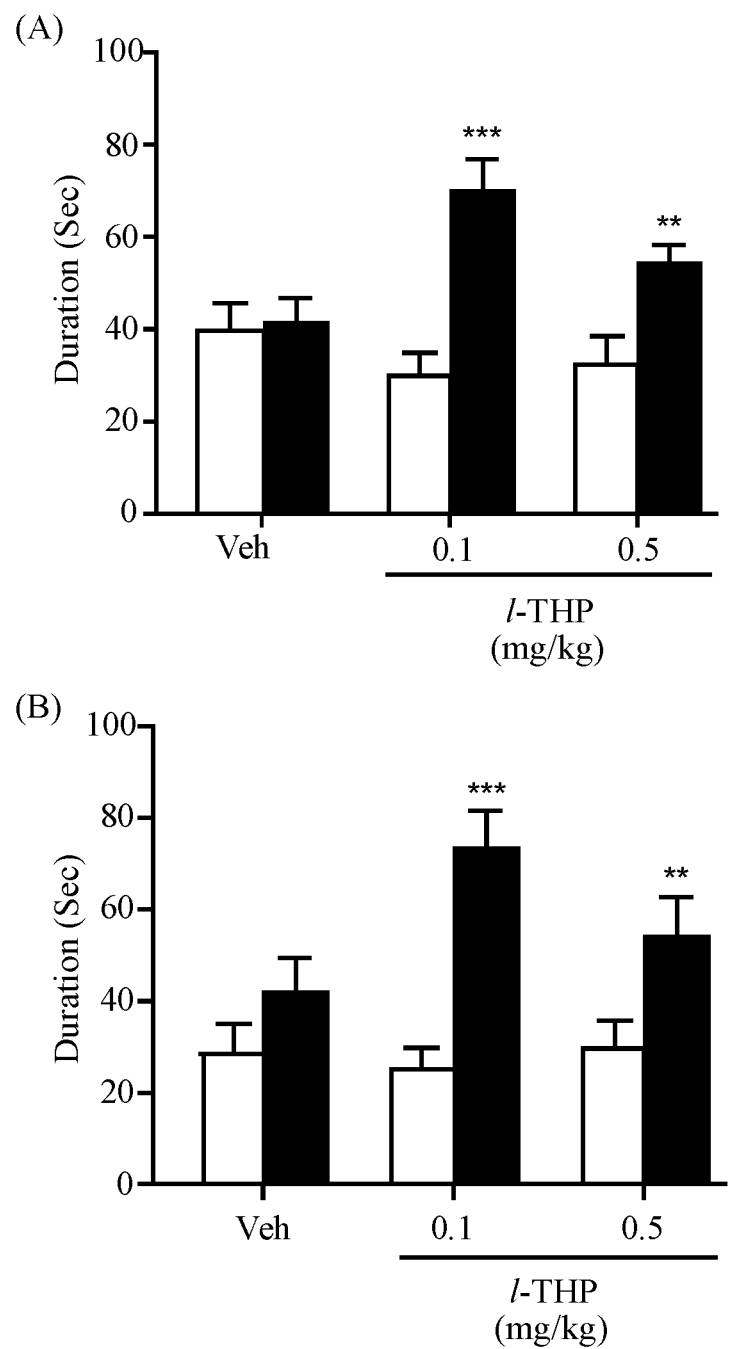
FIG. 3 shows bar graphs regarding Crawley's sociability and preference for social novelty test on mice for l-THP in the three-chamber-box apparatus. (A) Sociability test. Open bars represent duration of time spent by subject mouse with the empty container, and solid bars represent duration of time spent by subject mouse with container with another mouse, viz. stranger-1 mouse, in the three-chamber-box apparatus for mice treated with vehicle ("Veh"), mice treated with 0.1 mg/kg l-THP, and mice treated with 0.5 mg/kg l-THP. (B) Preference for social novelty test. Open bars represent duration of time spent by subject mouse with container holding the "familiar" stranger-1 mouse, and solid bars represent duration of time spent by subject mouse with container holding the "previously unencountered" stranger-2 mouse, in the three-chamber-box apparatus for mice treated with vehicle ("Veh"), mice treated with 0.1 mg/kg l-THP, and mice treated with 0.5 mg/kg l-THP. Data expressed as mean±S.E.M., n=12-20 mice per group. p<0.01 and *p<0.001 indicate significant difference from vehicle-treated ("Veh") group based on Newman-Keuls' test after one-way ANOVA.

In the sociability and preference for social novelty test, FIG. 3A shows that, when treated orally with vehicle only, the subject mice in the "Veh" group did not indicate any significant preference between container holding stranger-1 mouse and empty container with respect to the duration of time it spent with the two containers respectively. There was therefore no significant display of sociability toward stranger-1 mouse. However, when treated with either 0.1 mg/kg or 0.5 mg/kg l-THP, the subject mouse spent more time ($p<0.001$ for 0.1 mg/kg and $p<0.01$ for 0.5 mg/kg) with the stranger-1 mouse container than the empty container, thereby displaying a significant enhancement of sociability toward another mouse. FIG. 3B shows that the subject mice treated with vehicle only in the "Veh" group did not display any significant preference between the container containing the "familiar" stranger-1 mouse and the container holding the "previously unencountered" stranger-2 mouse. There was therefore no significant preference for social novelty. However, when treated with 0.1 mg/kg or 0.5 mg/kg l-THP, the mice showed preference for the novel stranger-2 mouse compared to the familiar stranger-1 mouse, thereby displaying significant ($p<0.001$ for 0.1 mg/kg and $p<0.01$ for 0.5 mg/kg) preference for social novelty. Consequently, the results of FIG. 3 indicate that treatment with an appropriate low dose of l-THP was capable of enhancing the attributes of sociability and preference for social novelty. Since depression, and deficits in sociability and preference for social novelty are common symptoms of individuals inflicted with bipolar disorder, the findings in FIG. 3 were indicative of the antidepression effects of l-THP Example 4: Test for Antimanic-Like Behavior Manic-like behavior was induced accomplished using the method of Pathak et al. (2015). Male ICR mice of 6 to 7 week were given daily injection of 1.8 mg/kg d-amphetamine (amphetamine-sensitized mice) or vehicle (0.9% NaCl vehicle treated, viz. mice unsensitized by amphetamine) for 5 days. Amphetamine was then withdrawn for 7 days. The locomotor activity test 'ZIL-2' apparatus (Beijing Institute of Materia Medica) employed consisted of a transparent plastic cylinder of 20 cm diameter×12 cm height equipped with six evenly spaced sets of infrared beam-photocell. The number of transitions made by the mouse across the beams as detected by the photocells was recorded automatically over a period of 5 minutes. The level of locomotor activity was scored by the number beam-crossings made by the mouse. In the test, amphetamine sensitized mice were randomly separated into groups (m=12-20 per group). The Amp group of mice received 0.9 mg/kg amphetamine injection 10 minutes prior to testing. The l-THP groups received oral l-THP (0.05, 0.1 and 0.2 mg/kg) 30 minutes prior to testing, and 0.9 mg/kg amphetamine injection 10 minutes prior to testing. The Veh mice received vehicle orally 30 minutes prior to testing and vehicle injection 10 minutes prior to testing.

Figure 4:
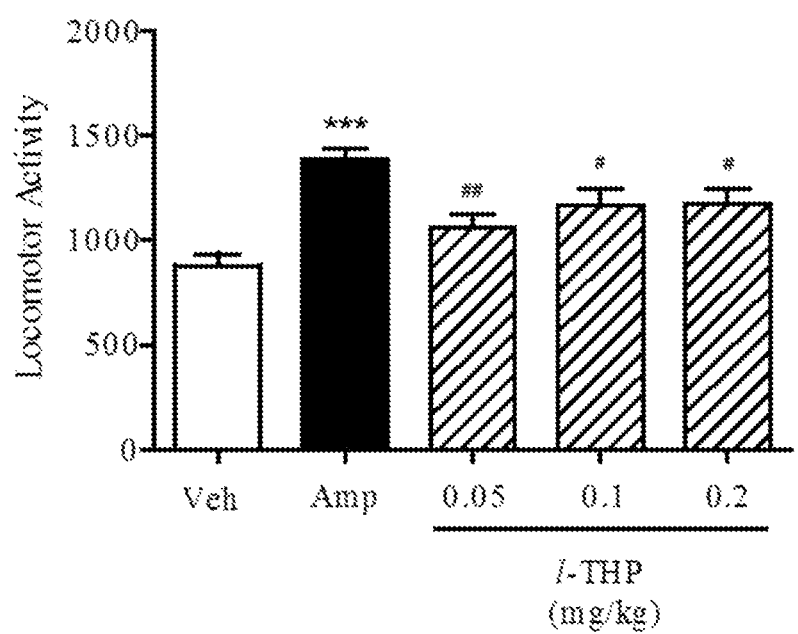
FIG. 4 shows graph bars regarding the antimanic effect of l-THP on manic-like behavior induced by amphetamine sensitization based on the level of locomotor activity monitored using a locomotor activity apparatus for mice unsensitized by amphetamine and treated with vehicle orally prior to locomotor activity test ("Veh"), mice sensitized by amphetamine and treated with vehicle prior to locomotor test ("Amp"), and mice sensitized by amphetamine and treated with oral l-THP (0.05-0.2 mg/kg) prior to locomotor test. n=12-20 mice per group. ***p<0.001 indicates significant difference between Amp group and Veh group; #p<0.05 and ##p<0.01 indicate significant difference between l-THP groups and Amp group based on Newman-Keuls' test after one-way ANOVA.

In the antimanic test, FIG. 4 shows that Amp mice displayed a significantly elevated level of locomotor activity compared to Veh mice. Oral l-THP at 0.05 mg/kg, 0.1 mg/kg or 0.2 mg/kg significantly reduced the level locomotor activity relative to the Amp mice. These findings indicated that oral l-THP exerted significant antimanic effects on the mice. Such antimanic effect points to utility in treatment of manic episodes. The combination of antidepressant, enhancement of sociability and preference for social novelty, and antimanic activity also points to anti-bipolar disorder activity.

Example 5: Elevated Plus-Maze Test

Elevated plus-maze test. Naïve male ICR mice 4 to 6 weeks of age were randomly separated into groups (n=15-20/group). Vehicle (0.9% NaCl), 0.01, 0.05, 0.1, 0.5, 1, 2 and 2.5 mg/kg dl-THP or l-THP, or 1 or 3 mg/kg diazepam was orally administered 45 minutes prior to experiment. The test apparatus consisted of four arms, 25 cm×5 cm each, extended from a center platform of 5 cm×5 cm in the shape of a plus sign. Two of the opposite arms were enclosed by 20 cm opaque high walls, making up the closed arms. The plus maze was elevated 40 cm off the ground. Each mouse was placed onto the center of the maze with head facing an open arm. The frequency and time spent in the open and closed arms were recorded for a period of 5 minutes. An arm entry was recorded when all four paws were inside the arm. Increased number of open-arm entries and percentage of time spent in them are indicative of an anxiolytic effect on the mice (Kalueff and Tuohimaa, 2004; Treit et al., 1993). In addition, the number of closed-arm entries provided an index of locomotor activity (Boguszewski and Zagrodzka, 2002). To test whether the anxiolytic effect elicited by l-THP can be blocked by the benzodiazepine (BZ) binding site antagonist flumazenil, naïve male 4-6 week old mice were randomly separated into three groups (n=12-20/group). The first group received vehicle (p.o.) 45 minutes prior to test and flumazenil (1.25 mg/kg i.p) 15 minutes prior to test, the second group received l-THP (1.0 mg/kg, p.o) 45 minutes prior to test and vehicle (i.p) 15 minutes prior to test, and the third group received l-THP (1.0 mg/kg p.o) 45 minutes prior to test and flumazenil (1.25 mg/kg i.p) 15 minutes prior to test.

Figure 5:
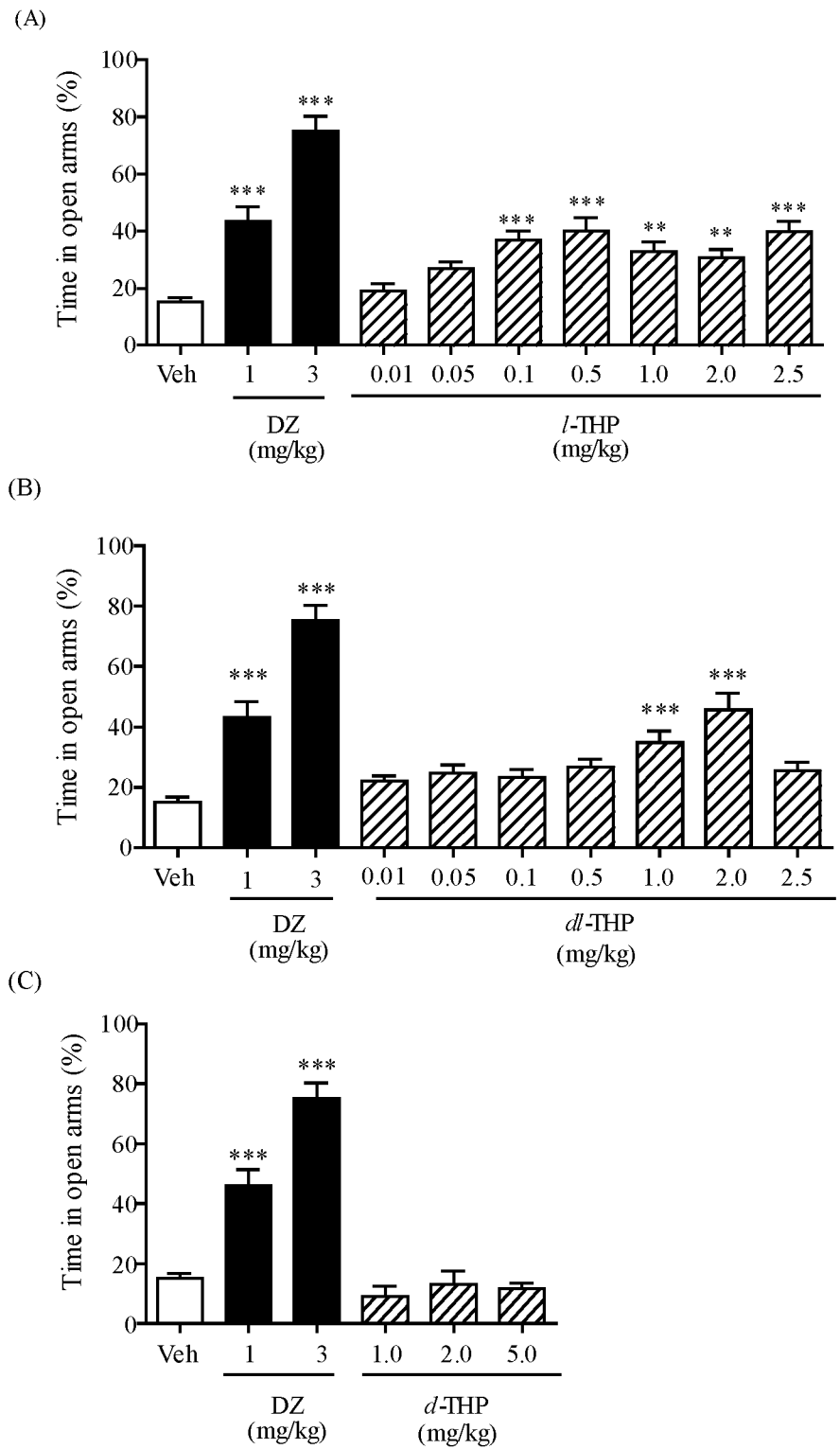
FIG. 5 shows bar graphs regarding the induction of anxiolytic effects in mice in elevated plus-maze test by (A) l-THP, (B) dl-THP and (C) d-THP. Data expressed as mean±S.E.M. of percentage of time spent in open arms during a 5-minute test period monitored 45 minutes after the oral administration of l-THP, dl-THP or dl-THP (0.01-5.0 mg/kg), diazepam (DZ, 1 or 3 mg/kg) or vehicle (Veh, 0.9% NaCl) and shown as shaded, solid or open bars respectively. n=12-20 mice per group. p<0.01 and *p<0.001 indicate significant difference from vehicle-treated ("Veh") group based on Newman-Keuls' test after one-way Anova.
Figure 7:
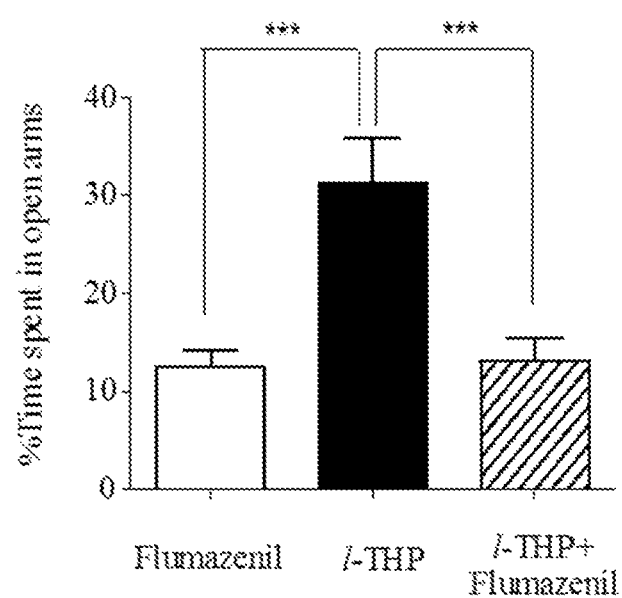
FIG. 7 shows bar graphs regarding the influence of flumazenil on anxiolytic effects of l-THP based on time spent in open arms in the elevated plus-maze test. Data expressed as mean±S.E.M. of time spent in open arms during a test period of 5 minutes. Where indicated, oral l-THP (1.0 mg/kg) was administered 45 minutes prior to test period, whereas flumazenil (1.25 mg/kg, i.p.) was administered 15 minutes prior to test period. Open, solid and shaded bars represent mice receiving flumazenil i.p. only, mice receiving oral l-THP only, and mice receiving flumazenil i.p. plus oral l-THP respectively. n=12-20 mice per group. ***p<0.001 indicates significant difference between two treatment groups joined by line based on Newman-Keuls' test after one-way Anova.

In the elevated plus maze test, l-THP induced a significant increase in time spent in the open arms indicative of an anxiolytic effect with $p<0.01$ on the mice at 1.0 mg/kg and 2.0 mg/kg, and $p<0.001$ at 0.1 mg/kg, 0.5 mg/kg and 2.5 mg/kg. By comparison, dl-THP induced a significant increase in time spent in the open arms only at higher doses, with $p<0.001$ at 1.0 mg/kg and 2.0 mg/kg. The anxiolytic benzodiazepine site agonist Diazepam (DZ) exhibited significant anxiolysis with $p<0.001$ at 1 and 3 mg/kg (FIG. 5). The inhibition of the anxiolytic effect of l-THP by the BZ-site antagonist flumazenil of $GABA_A$ receptors (FIG. 7) confirmed the well-known involvement of $GABA_A$ receptors in anxiolysis.

Example 6: Locomotor and Myorelaxant Side Effects

Male ICR mice of 4 to 6 weeks were randomly separated into groups (n=15-20 per group). Vehicle (0.9% NaCl), 0.01-2.5 mg/kg dl-THP or l-THP, and 1 and 3 mg/kg diazepam were orally administered 45 minutes prior to test. Locomotor activity was measured based on crossings of infrared beams. Mice treated with l-THP or dl-THP did not bring about any significant deficit in locomotion up to 2.5 mg/kg. In contrast, 3 mg/kg DZ induced significant decrease ($p<0.05$) in locomotor activity (Table 1). Myorelaxant activity was measured using the horizontal wire test. In this test, mouse was lifted by the tail and allowed to grasp onto a horizontally strung wire (1 mm diameter, 20 cm long and placed 20 cm above the table) with their forepaws and released. For each mouse, the number of falls in 60 seconds was recorded. When tested in the horizontal-wire test, l-THP or dl-THP up to 10 mg/kg did not induce any significant myorelaxant effect in terms of increased number of falls. Both l-THP and dl-THP at 30 mg/kg induced significant ($p<0.01$) myorelaxant effect, and DZ at 3 mg/kg induced significant ($p<0.05$) myorelaxant effect.

Previously it was found that dl-THP upon oral administration induced selective anxiolytic effects in mice in the elevated plus maze test based on significant increase in entries into open arms without significant change in entries into closed arms (Leung 2003). In the invention, oral l-THP was found to be a more potent agent for anxiolysis, active at as low as 0.1 mg/kg, than oral dl-THP which required a minimum 1.0 mg/kg dose for activity (FIG. 5).

Oral l-THP elicited antidepressant effect based on the immobility time in the tail suspension test starting from 0.5 mg/kg. In contrast, oral dl-THP elicited antidepressant effects only starting at the higher dose level of 2.0 mg/kg (FIG. 2). As well, 0.1 mg/kg and 0.5 mg/kg oral l-THP both enhanced sociability (FIG. 3A) and preference for social novelty (FIG. 3B). Furthermore, oral l-THP at 0.05 mg/kg, 0.1 mg/kg and 0.2 mg/kg induced antimanic effects on mice (FIG. 4). The antimanic effect indicates utility of l-THP for treatment of manic episodes. The combination of antidepressant effect, enhancement of sociability and preference for social novelty, and antimanic activity further indicates that oral l-THP can provide useful treatment for bipolar disorders. Importantly, the range of active l-THP dosages for these different kinds of pharmacological effects of l-THP in the range of 0.05-5.0 mg/kg were well below l-THP dosages that would elicit significant locomotor activity alteration or myrelaxant side effects (FIGS. 8 and 9).

Besides being a constituent of Rhizoma *Corydalis yanhusuo* WT Wang, which has long been employed as a medicinal herb in Chinese medicine, l-THP has been an approved pharmaceutical in China for analgesia, as either 30 mg or 60 mg Rotundine Tablets for adult dosage of 60-120 mg/kg, or 2 ml:60 mg Rotundine Sulfate Injection (Chinese Pharmacopoeia 2015). For a 60 kg human subject, a 60-120 mg dose is equivalent to 1.0-2.0 mg/kg. Since the pharmacological equivalent dose of pharmaceuticals for a human is 37/3-fold that of a mouse (Reagan-Shaw et al, 2008) based on the body surface area (BSA) normalization method suggested by the Food and Drug Administration (Center for Drug Evaluation and Research, 2002), a 1.0-2.0 mg/kg dose for humans translates to 12.3-24.6 mg/kg for mice (Reagan-Shaw et al, 2008). Accordingly, the Rotundine dose level is ~12-25× the dose level found in the present study for the induction of maximal antidepressant effect (FIG. 2A), or ~120-250× the dose level for the induction of maximal anxiolytic effect (FIG. 5A), by l-THP in mice.

The low dosage requirement for the induction of antidepressant, enhancement of sociability and preference for social novelty, antimanic, anti-bipolar disorder and anxiolytic effects by l-THP compared to the higher dosage requirement for analgesia suggests that the pathways mediating the induction of antidepressant and anxiolytic effects by l-THP might not be identical to the pathways mediating its analgesic effects. This is in accord with the finding that administration of 10, 20 and 40 mg/kg i.p. l-THP, produced dose-dependent antinociceptive effects mediated by D2 receptors in rats (Hu and Jin, 1999; Chu et al, 2008). The 10-40 mg/kg dosage range for antinociception in rats, translating to 20-80 mg/kg. i.p. in mice (Center for Drug Evaluation and Research, 2002), viz. ~20-80× the dose level for induction of maximal antidepressant effect (FIG. 2A), or >200× the dose level for induction of anti-manic effect (FIG. 4A) in mice.

It has been reported that l-THP also ameliorated the anxiety and depression-related symptoms of post-traumatic stress disorder (PTSD) in rats: daily administration of 50 mg/kg i.p., but not 10 or 20 mg/kg i.p. l-THP induced a significant antidepressant effect based on either sucrose intake or immobility time in the forced swimming test, and a significant anxiolytic effect based on the elevated plus-maze test (Lee et al, 2014). This requirement for 50 mg/kg i.p. l-THP for such treatment of PTSD translates to a 100 mg/kg i.p. equivalent dosage in mice, viz. >50× the oral dose of l-THP for antidepression effect or >100× the oral dose of l-THP for anti-manic effect in mice under non-PTSD conditions (FIGS. 2A and 4A). These high l-THP dosage requirements for antidepression and anxiolysis in PTSD, comparable to the dosage requirements for analgesia and antinociception but much higher than the l-THP dosage requirements for antidepression, anti-manic effect and anxiolysis under non-PTSD conditions suggest that the induction of antidepressant, anti-manic and anxiolytic effects of l-THP under non-PTSD conditions are mediated by neurological pathways that are non-identical to those mediating analgesia, antinociception, antidepression and anxiolysis in PTSD by l-THP. This is in accord with Diagnostic and Statistical Manual of Mental Disorders Fifth Edition (DSM-5 American Psychiatric Association) which classifies PTSD under 'Trauma- and Stressor-Related Disorder', distinct from 'Depression Disorders', 'Bipolar and Related Disorder', and 'Anxiety Disorders'.

Accordingly, based on dosage requirements, two broad categories of potential therapeutic effects of l-THP are recognized. The high-dosage effects include the analgesia effect, antinociception effect, and antidepressant and anxiolysis activities for the treatment of 'post-traumatic stress disorder' as defined in DSM-5. The low-dosage effects include antidepressant activity and enhancement of sociability and preference for social novelty for the treatment of 'depression disorders', and together with antimanic effect for anti-bipolar disorder activity for treatment of 'manic episodes' and 'bipolar disorders', and anxiolytic activity for the treatment of 'anxiety disorders' as defined in DSM-5. On this basis, the dosage of l-THP required for the treatment of depression disorders, bipolar disorders, manic episodes and anxiety disorders as defined in DSM-5 would be of the order of 0.5-5% of the dosage of l-THP approved for Rotundine in China for analgesia, thereby enhancing extensively the potential safety of the administered dosages. Moreover, the lack of altered locomotor activity in mice following the oral administration of l-THP at 2.5 mg/kg (FIG. 8), and the lack of myorelaxant effect on mice following the oral administration of l-THP up to 10 mg/kg (FIG. 9) also suggest that oral l-THP could be safe up to 2.5 mg/kg, covering the effective dosage ranges needed for antidepressant, antimanic, antibipolar disorder or anxiolytic applications. This is supported by the earlier reports that l-THP given to mice at 6.25, 12.5, and 18.75 mg/kg i.g. did not affect locomotor activity (Liu et al, 2005); and that, although administration of 10 mg/kg i.p. l-THP inhibited locomotion in rats, its administration at the lower dose of 3 mg/kg i.p. in rats, which would be equivalent to 6 mg/kg in mice, failed to do so (Xi et al, 2007). Overall, therefore, l-THP is effective for the treatment of depression disorders, manic episodes, bipolar disorders and anxiety disorders.

When introducing elements of the invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

The following references have been cited in the foregoing paragraphs:

Begley C E, Annegers J F, Swann A C et al (2001). The life time cost of bipolar disorder in the US: an estimate for new cases in 1998. Pharmacoeconomics 19 (5 Pt 1), 483-495.

Bei W J, Mantsch J R (2012). L-tetrahydropalmatine: a potential new medication for the treatment of cocaine addiction. *Future Med Chem* 4: 177-186.

Boguszewski P, Zagrodzka J (2002). Emotional changes related to age in rats—a behavioral analysis. *Behav Brain Res* 133, 323-332.

Center for Drug Evaluation and Research (2002). Estimating the safe starting dose in clinical trials for therapeutics in adult healthy volunteers, *Center for Biologics Evaluation and Research, U.S. Food and Drug Administration*: Rockville, Md., USA. Chinese Pharmacopoeia Committee (2015). *Pharmacopoeia of People's Republic of China* (Vol. II), $1^{st}$ edn. China Medical Science & Technology Press: Beijing pp 656-657.

Chu H, Jin G, Friedman E, Zhen X (2008). Recent development in studies of tetrahydroprotoberberines: mechanism in antinociception and drug addiction. *Cell Mol Neurobiol* 28: 491-499.

Cusi A M, Nazarov A, Holshausen K et al (2012). Systematic review of the neural basis of social cognition in patients with mood disorders. *J Psychiatry Neurosci* 37, 154-169.

Depp C A, Mauscbach B T, Harvey P D et al. (2010). Social competence and observer-rated social functioning in bipolar disorder. *Bipolar Disorder* 12, 843-850.

DSM-5. Diagnostic and Statistical Manual of Mental Disorders $5^{th}$ Edition (2013). American Psychiatric Association.

Hu J Y, Jin G Z (1999). Supraspinal D2 receptor involved in antinociception induced by l-tetrahydropalmatine. Zhongguo Yao Li Xue Bao 20: 715-719.

Huen M S, Hui K M, Leung J W, Sigel E, Baur R, Wong J T et al (2003). Naturally occurring 2'-hydroxyl-substituted flavonoids as high-affinity benzodiazepine site ligands. *Biochem Pharmacol* 66: 2397-2407.

dJang Y, Lee S H, Lee B et al. (2015). TRPM2, a susceptibility gene for bipolar disorder, regulates glycogen synthase kinase-3 activity in the brain. *J. Neuroscience* 35, 11811-23.

Kalueff A V, Tuohimaa P (2004). Experimental modeling of anxiety and depression. *Acta neurobiologiae experimentalis* 64: 439-448.

Kaidanovich-Beilin O, Lipina T, Vukobradovic I, et al (2011). Assessment of social interaction behavior. *J Visualized Expt* 48: e2473, doi:10.3791/2473.

Kostryrko A, Hauser J, Rybakowski J K, Trzeciak W H (2006). Screening of chromosomal region 21q22.3 for mutations in genes associated with neuronal Ca2+ signalling in bipolar affective disorder. *Acta Biochim Pol* 53, 317-320.

Leahy R L, (2007). Bipolar disorder: causes, contexts and treatments. *J Clin Psychol: in Session* 63: 417-424.

Leung W C, Zheng H, Huen M, Law S L, Xue H (2003). Anxiolytic-like action of orally administered dl-tetrahydropalmatine in elevated plus-maze. *Prog Neuropsychopharmacol Biol Psychiatry* 27: 775-779.

Lee B, Sur B, Yeom M, Shim I, Lee H, Hahm D H (2014). L-tetrahydropalmatine ameliorates development of anxiety and depression-related symptoms induced by single prolonged stress in rats. *Biomol Ther* 22: 213-222.

Liu Y L, Liang J H, Yan L D, Su R B, Wu C F, Gong Z H (2005). Effects of l-tetrahydropalmatine on locomoter sensitization to oxycodone in mice. *Acta Pharma Sinica* 26: 533-538.

Liu Y L, Yan L D, Zhou P L, Wu C F, Gong Z H (2009). Levo-tetrahydropalmatine attenuates oxicodone-induced conditioned place preference in rats. *European journal pharmacology* 602: 321-327.

Mantsch J R, Li S J, Risinger R, Awad S, Katz E, Baker D A et al (2007). Levo-tetrahydropalmatine attenuates cocaine self-administration and cocaine-induced reinstatement in rats. *Psychopharmacology* 192: 581-591.

McQuillin A, Bass N J, Kalsi et al (2006) Fine mappring of a susceptibility locus for bipolar and genetically related unipolar affective disorders, to a region containing the C21ORF29 and TRMP2 genes on chromosome 21q22.3. *Mol Psychiatry* 11, 134-142.

Moy S S, Nadler J J, Perez A, Barbaro R P, Johns J M, Magnuson T R, Piven J, Crawley J N (2004). Sociability and preference for social novelty in five inbred strains: an approach to assess autistic-like behavior in mice. *Genes Brain Behav* 3, 287-302.

Reagan-Shaw, S, Nihal, M, Ahmad, N (2008). Dose translation from animal to human studies revisited. *FASEB J* 22: 659-661.

Rotundine Tablet (product No. H14020787), Yunpeng Shanxi Pharmaceutical Co. Ltd. Stem L, Chermat R, Thierry B, Simon P (1985). The tail suspension test: a new method for screening antidepressants in mice. *Psychopharmacology* 85: 367-370.

Treit D, Menard J, Royan C (1993). Anxiogenic stimuli in the elevated plus-maze. *Pharmacol Biochem Behav* 44: 463-469.

Xu S X, Yu L P, Han Y R, Chen Y, Jin G Z (1989). Effects of tetrahydroprotoberberines on dopamine receptor subtypes in brain. *Acta Pharmacologica Sinica* 10, 104-110.

Yuan C S, Mehendale S R, Wang C Z, Aung H H, Jiang T, Guan X et al (2004). Effects of Corydalis yanhusuo and *Angelicae dahuricae* on cold pressor-induced pain in humans: a controlled trial. *J Clin Pharmacol* 44, 1323-1327.

Zhao N, Chen Y, Zhu J, Wang L, Cao G, Dang Y et al (2014). Levo-tetrahydropalmatine attenuates the development and expression of methamphetamine-induced locomotor sensitization and the accompanying activation of ERK in the nucleus accumbens and caudate putamen in mice. *Neuroscience* 258: 101-110.

What is claimed is:

1. A method for treating a depression disorder, a bipolar or bipolar-related disorder, or a manic episode in a patient in need thereof comprising administering an effective amount to the patient of levorotatory-tetrahydropalmatine or a pharmaceutical composition comprising the effective amount of the levorotatory-tetrahydropalmatine.

2. The method of claim 1, wherein the depression disorder is treated.

3. The method of claim 1, wherein the bipolar or bipolar-related disorder is treated.

4. The method of claim 1, wherein the manic episode is treated.

5. The method of claim 1, wherein the patient is not in need of treatment for post-traumatic stress disorder.

6. The method of claim 2, wherein the effective amount is from about 2 trig to about 15 mg per kg body weight administered.

7. The method of claim 2, wherein the effective amount is administered through oral delivery.

8. The method of claim 2, wherein the effective amount is administered through transdermal delivery.

9. The method of claim 3, wherein the effective amount is from about 0.1 mg to about 15 mg per kg body weight administered.

10. The method of claim 3, wherein the effective amount is administered through oral delivery.

11. The method of claim 3, wherein the effective amount is administered through transdermal delivery.

12. The method of claim 4, wherein the effective amount is from about 0.1 mg to 2 mg per kg body weight administered.

13. The method of claim 4, wherein the effective amount is administered through oral delivery.

14. The method of claim 4, wherein the effective amount is administered through transdermal delivery.

15. The method of claim 1, wherein the effective amount is administered in a single aliquot.

16. The method of claim 1, wherein the effective amount is administered in two or more aliquots.

* * * * *